United States Patent [19]

Björk et al.

[11] Patent Number: 4,624,953
[45] Date of Patent: Nov. 25, 1986

[54] 1-PIPERAZINOCARBOXYLATES AND PHARMACEUTICAL COMPOSITIONS CONTAINING THEM

[76] Inventors: Anders K. Björk, Svalvägen 9, S-237 00 Bjärred; Erik G. Christensson, Nils Bjelkegatan 3A, S-222 20 Lund, both of Sweden

[21] Appl. No.: 519,761

[22] PCT Filed: Nov. 30, 1982

[86] PCT No.: PCT/SE82/00408
§ 371 Date: Jul. 28, 1983
§ 102(e) Date: Jul. 28, 1983

[87] PCT Pub. No.: WO83/01950
PCT Pub. Date: Jun. 9, 1983

[30] Foreign Application Priority Data
Dec. 2, 1981 [SE] Sweden .................. 8107201

[51] Int. Cl.[4] .................. A61K 31/495; C07D 295/10
[52] U.S. Cl. .................. 514/255; 544/377; 544/389
[58] Field of Search .......... 544/377, 389; 424/250; 514/255

[56] References Cited
U.S. PATENT DOCUMENTS 2,819,269 1/1958 Weston et al. ................ 544/389
4,112,091 9/1978 Nesvadba et al. ............. 544/389
4,252,804 2/1981 Joullié et al. ................ 544/389

OTHER PUBLICATIONS

Collection Czechoslov. Chem. Commun. 1980, 45 (11), 3182-89 published Mar. 10, 1980.
Arzneimittel-Forsch. Drug. Res., 27(1), No. 4, (1977) pp. 828-832, W. Meuldermans, et al., "In Vitro Metabolism of Lidoflazine by Rat and Dog Liver Fractions".
Chemical Abstracts, vol. 85 (1976), abstract No. 33082m, Japan Kokai 76 08, 283.
Bjoerk, et al., "Chemical Abstracts", vol. 99, 1983, col. 99:158462f.

Primary Examiner—Glennon H. Hollrah
Assistant Examiner—James H. Turnipseed
Attorney, Agent, or Firm—Scully, Scott, Murphy & Presser

[57] ABSTRACT

Compounds having the general formula

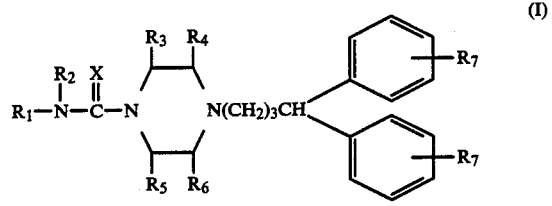

(I)

as herein defined and pharmaceutically acceptable acid addition salts thereof. Pharmaceutical compositions containing said compounds. Methods of treatment of humans and animals by such compounds and compositions.

6 Claims, No Drawings

1-PIPERAZINOCARBOXYLATES AND PHARMACEUTICAL COMPOSITIONS CONTAINING THEM

FIELD OF INVENTION

The present invention is concerned with a novel series of diphenylbutyl-1-piperazinocarboxylates having valuable properties for treatment of mental disorders the preparation of such compounds, pharmaceutical compositions containing such compounds and the use of the compounds in human and veterinary medicine.

PRIOR ART

Japan Kokai 76 08,283 (CA 85: 33082m) describes as having analgetic properties piperazine derivatives of formula:

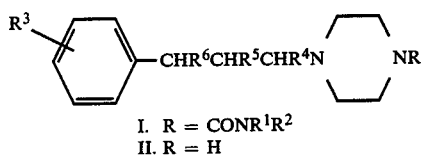

I. R = CONR$^1$R$^2$
II. R = H wherein R$^1$, R$^2$=H, alkyl, cycloalkyl, substituted Ph, NR$^1$R$^2$=heterocyclyl; R$^3$=H, halo, alkyl, alkoxy, CF$_3$, OH; R$^{4-6}$=H, alkyl, substituted Ph, benzyl. Swedish patent application No. 7908701-1 describes as having psychotropic properties piperazine derivatives of formula:

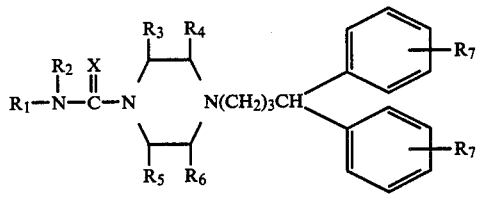

wherein R$_1$ and R$_2$ are groups independently selected from the group of hydrogen, alkyl straight or branched chains having from 1 to 10 carbon atoms, cycloalkyl having from 3 to 8 carbon atoms, aralkyl having from 7 to 9 carbon atoms, alkenyl having from 2 to 10 carbon atoms, phenyl unsubstituted or substituted by one to three substituents selected from halogen, including F, Cl and Br, lower alkyl having from 1 to 5 carbon atoms, lower alkoxy having from 1 to 5 carbons atoms, amine unsubstituted or substituted by one or two lower alkyl groups having from 1 to 5 carbon atoms, —CF$_3$ and —CN groups, R$_3$, R$_4$, R$_5$ and R$_6$ are groups independently selected from hydrogen, lower alkyl having from 1 to 3 carbon atoms and phenyl, R$_7$ is a group selected from hydrogen, halogen including F, Cl and Br, lower alkoxy having from 1 to 3 carbon atoms and —CF$_3$ groups, and X is O or S.

Collect. Czech. Chem. Commun. 1980, 45 (11), 3182-89 mentions as an intermediate in a series of reactions the compound of formula:

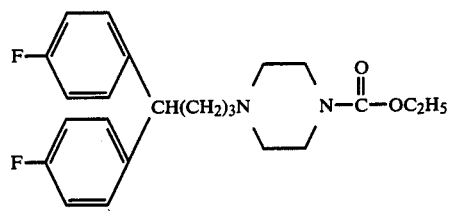

All the compounds A and B described in the above mentioned Japan Kokai No. 76 08,283 and Swedish patent application No. 7908701-1 are 1-piperazinecarboxamide derivatives and chemically not related to the compounds according to the present invention which are 1-piperazinecarboxylate derivatives.

Thus, the compounds A and B are chemically amides while the compounds according to the present invention are carboxylic esters.

Compound C is as the compounds according to the present invention a 1-piperazinecarboxylate derivative. However, said compound is only shown by means of a formula and not identified by any physical constant. Furthermore, there are no statements at all concerning any pharmacodynamic property of said compound.

DESCRIPTION OF THE INVENTION

It has now been found that compounds of formula I:

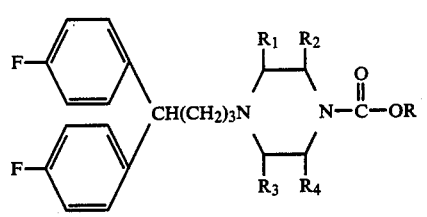

wherein R is alkyl straight or branch chained having from 1 to 10 carbon atoms, cycloalkyl having from 3 to 8 carbon atoms, aralkyl having from 7 to 9 carbon atoms or phenyl unsubstituted or substituted by one to three F, Cl, Br, lower alkyl having from 1 to 5 carbon atoms, lower alkoxy having from 1 to 5 carbon atoms, alkylenedioxy having from 1 to 3 carbon atoms, —CF$_3$ or —CN substituents, R$_1$–R$_4$ are independently H, CH$_3$, C$_2$H$_5$ with cis or trans configuration provided that only two of them are other than hydrogen, and pharmaceutically acceptable salts thereof unexpectedly exhibit valuable properties for treatment of mental disorders such as psychoses and aggression rendering them useful for treatment of humans and animals.

The compounds of formula (I) can generally be prepared

A(a) by reacting an appropriate chloroformate of formula (II)

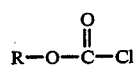

wherein R is as previously defined, with a 1-(4,4-diarylbutyl)-piperazine of formula (III)

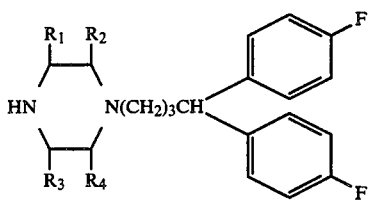

wherein $R_1$–$R_4$ are as previously defined, to form a compound of formula (I) or A(b) by reacting a 1-piperazinocarboxylate of formula (IV)

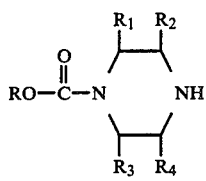

with a 4-substituted 1,1-diarylbutane of formula V

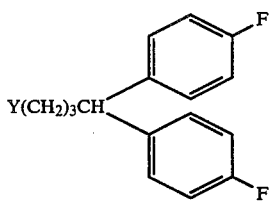

wherein R and $R_1$–$R_4$ are as above defined and Y is halogen, preferably Br or another reactive group, e.g. a mesyl or tosyl ester group, to form a compound of formula I.

The 1-piperazinocarboxylates of formula IV employed in the processes according to the invention may be prepared by a sequence of operations starting with:

B(a) a reaction between a chloroformate

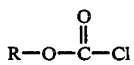

and a 1-benzyl-piperazine of formula IV

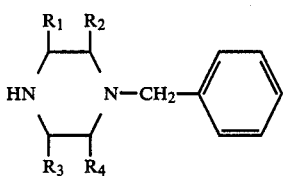

in chloroform or the like to form a compound of formula VII

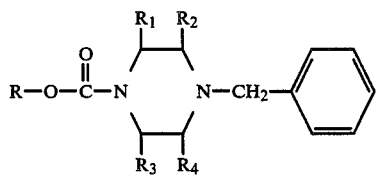

The compound of formula VII is hydrogenated over a noble metal catalyst to give the compound of formula IV.

In sequence A(a) reaction may be carried out following standard N-acylation procedures. The compound of formula III (synthesized according to Neth. Appln. No. 6,507,312) is reacted with a chloroformate of formula II in an appropriate reaction-inert organic solvent, e.g., diethyl ether, chloroform, toluene and the like to form the compounds of formula I. The mixture is reacted over a wide range of temperatures from about 10° C. to about 110° C., although it is possible to employ temperatures above and below this range. The reaction may be carried out in the presence of an acid acceptor, such as triethylamine, to sequester hydrogen chloride which is liberated in the reaction.

In sequence A(b) the compound of formula IV is reacted with a compound of formula V (synthesized according to French Patent No. M 3695) in a suitable solvent, e.g. a lower alkanol, such as methanol, ethanol, n-butanol and the like, in the presence of an acid acceptor, i.e. an appropriate base, e.g. an alkali metal carbonate or bicarbonate, which may be utilised to bind the acid that is liberated during the course of the reaction to give the compound of formula I. Elevated temperatures may be employed to enhance the rate of reaction.

The potency of the compounds of formula (I) and their pharmaceutically active acid addition salts as agents for treatment of mental disorders is clearly evidenced by the results obtained in the following tests.

Test I: Isolation-induced aggressive behaviour test

Male mice subjected to prolonged isolation develop aggressive behaviour against each other when paired (Yen, C. Y. et al., Arch. Int. Pharmacodyn. 123, 179, (1959); Valzelli, L., Adv. Pharmacol. 5, 79 (1967)). All clinically used neuroleptics and antidepressants studied in this test inhibit this aggressive behaviour although their activity may differ. Also anxiolytic drugs, e.g. diazepam, are active on this kind of aggressive behaviour. The clinical correlation of this test indicates tranquillizing and anxiolytic activities as well as antiaggressive properties as such (Duncan, R. L. et al., J. Med. Chem. 13, 1 (1970)).

This type of aggression is interesting because it is known that this kind of emotional behaviour might be located in limbic structures in the brain (MacLean, P. D., Psychosom. Med. 11, 338 (1949)).

Every week male NMRI mice, weighing 20–22 g, were isolated in Makrolon cages for three weeks with diet and water ad libitum. A piece of cardboard was placed between the cages to prevent visual contact.

To test aggressiveness the mice were paired in a neutral area, a beaker (14 cm high and diameter 14 cm). A pair is considered aggressive if both the animals show clear signs of fighting within 5 min. This fighting is characterized by biting and vocalization. As soon as fighting is seen, the mice are separated and brought to their home cage. (Every second mouse is marked.) If only one of two mice exhibit aggressive behaviour the aggressive one is paired with another to make a well matched, aggressive pair. Animals showing no aggression are discarded. The frequency of paired mice exhibiting fighting varies from 50–100 percent depending on the time of the year. The test substance is administered s.c. (0.2–0.4 ml/20 g). The mice are paired 0.5 h after the injection for trials of 5 min. duration.

The ED$_{50}$-value (mg/kg) reported is the dose inhibiting aggressive behaviour among 50 percent of the pairs 0.5 hour after drug administration.

Test 2: Conditioned avoidance response (CAR)

The effect of the test compounds on CAR was evaluated in a shuttle box, manufactured by Ugo Basile, Italy. The female rats, weighing 150 g, were trained to avoid an electric shock (unconditioned stimulus—US) by escaping from one compartment to the other when the light from a 15 W lamp switched on (conditions stimulus—CS). When they responded to the CS, a conditioned response (CR) was considered to have been elicited.

Rats showing a stable CR of more than 80% after a three weeks' training program were used in the experiments. Groups of six rats were subcutaneously administered with various doses of the test compounds. 1½ and 4 hours after the administration each rat was placed in the experimental box and the effect on CR was evaluated. ED$_{50}$-values refer to the dose inhibiting CR in 50% of the animals.

The mechanisms regulating conditioned responses are very complex. Both catecholaminergic and hormonal factors are of importance.

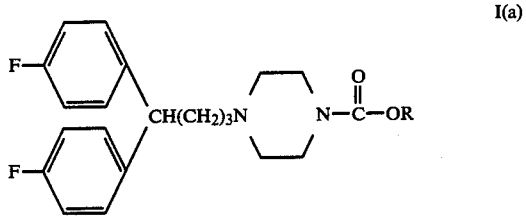

I(a)

TABLE 1

| Isolation induced aggressive behaviour. | | |
|---|---|---|
| Compound | R | ED$_{50}$, mg/kg s.c. |
| I (a) | Me | 6 |
| Chlorpromazine[a] | | 1.4 |
| Thioridazine[b] | | 5 |
| Amitriptyline[c] | | 5 |
| Diazepam[d] | | 6.7 |

[a]The Merck Index, 9th Ed., 2175
[b]The Merck Index, 9th Ed., 9098
[c]The Merck Index, 9th Ed., 504
[d]The Merck Index, 9th Ed., 2961

TABLE 2

| Conditioned avoidance behaviour. | | | |
|---|---|---|---|
| | | ED$_{50}$ mg/kg, s.c. | |
| Compound | R | 1.5 hr | 4 hr |
| I (a) | Me | 45 | 12 |
| Chlorpromazine[a] | | 3.5 | 5.2 |
| Thioridazine[b] | | 41 | 40 |

[a]The Merck Index, 9th Ed., 2175
[b]The Merck Index, 9th Ed., 9098

The compound listed in table 1 and 2 is not given for the purpose of limiting the invention thereto but only to exemplify the useful pharmacological activities of compounds within the scope of formula (I).

The subject compounds are particularly valuable since their anti-psychotic and anti-aggressive action is substantially free from undesirable side-effects such as sedation, catalepsy and extrapyramidal dysfunction associated with currently used antipsychotics such as the phenothiazines and butyrophenones.

Until recently the therapeutic efficacy of the neuroleptics was considered to be closely associated with the extrapyramidal motor action and was evaluated in terms of their ability to produce a characteristic catalepsy in animals. It is however now believed that the extrapyramidal dysfunction is caused by blockade of the dopamine receptors in the striatum (Hornykiewicz, O. in Handbook of Neurochemistry, Lajtha, A. ed. Plenum Press New York 1973 p. 465) whereas the antipsychotic activity is due to a similar interaction in the mesolimbic area of the brain (Anden, N. E. et al. J. Pharm. Pharmacol., 25, 346 (1973); Bertholini, G. ibid. 28, 429 (1976)). In contrast to typical neuroleptics the subject compounds antagonize the stereotypy induced in rats by amphetamine only at high doses.

Furthemore, also in another respect the compounds of formula (I) have an atypical mode of action, viz. the effect on exploratory behaviour, i.e. the climbing test in mice, in which test the compounds do not show effect even at high doses.

The compounds have no or very few autonomical side effects and a low degree of toxicity.

The formula I bases are convertible to therapeutically active non-toxic acid addition salts by treatment with an appropriate acid, e.g. an inorganic acid, such as a hydrohalic acid, especially hydrochloric and hydrobromic acid, or sulfuric acid, nitric acid, phosphoric acid and the like, or an organic acid such as acetic, propionic, glycolic, lactic, malonic, succinic, fumaric, tartaric, citric and the like acids. Conversely, the salt form can be converted by treatment with alkali into the free base form.

The compounds of formula (I) and their pharmaceutically active acid addition salts are useful in the control of psychotic and aggressive conditions in humans. For example they are useful for the prophylaxis and/or treatment of schizophrenia, mania or senile, involutional or organic psychoses as well as depressive psychosis.

The new compounds may also be used in the prophylaxis and treatment of aggressive behaviour, which may be associated with mentally retarded and/or behaviourally disturbed patients and other forms of aggression of either known or unknown etiology.

The new compounds are very useful in the treatment of aggressive behaviour in animals, especially in pigs, and also in promoting the development of a natural hierarchy in groups of animals without bursts of aggression and in calming of anxious and stressed animals.

Effective quantities of any of the foregoing pharmacologically active compounds of formula (I) may be administered to a human being or animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier or excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards, preferably 25, 50 or 100 milligrams or even higher depending on the condition to be treated and the age and weight of the patients as well as the response to the medication.

The unit dose may be from 0.1 to 200 milligrams, preferably from 10 to 50 milligrams. Daily dosages should preferably range from 10 milligrams to 400 milligrams. The exact individual dosages as well as daily dosages will, of course, be determined according to standard medical principles under the direction of a physician or veterinarian.

The following formulations are representative for all of the pharmacologically active compounds of this invention.

Example of a suitable capsule formulation:

|  | per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

|  | per tablet, mg |
|---|---|
| Active ingredient, as salt | 10 |
| Potato starch | 90 |
| Colloidal silica | 10 |
| Talc | 20 |
| Magnesium stearate | 2 |
| 5% Aqueous solution of gelatin | 25 |
| Total | 157 |

The pharmaceutical preparations may also contain therapeutically useful substances other than the pharmacologically active compounds of formula I.

The following examples are intended to illustrate the present invention without limiting the scope thereof.

EXAMPLE 1

1-Carbomethoxy-4-benzylpiperazine

To a solution of 35.2 g (0.20 mole) of 1-benzylpiperazine in 100 ml of $CHCl_3$ was added dropwise over a period of 30 minutes a solution of 17.0 g (0.18 mole) of methyl chloroformate in 110 ml of $CHCl_3$. The mixture was allowed to reflux during 2.5 hours and was made basic with 16 g of sodium hydroxide in 100 ml of water. The nonaqueous layer was separated, dried over magnesium sulphate and concentrated. The residue was distilled b.p. 108°–10° C. at 0.1–0.2 mmHg to give 34.5 g of 1-carbomethoxy-4-benzylpiperazine.

EXAMPLE 2

1-Carbomethoxypiperazine 34.0 g (0.15 mole) of 1-carbomethoxy-4-benzylpiperazine dissolved in 300 ml of ethanol was treated with hydrogen over a palladium catalyst at 40 psi and room-temperature for 24 hours. The catalyst was removed by filtration and the solvent removed under reduced pressure. The residue was distilled, b.p. 70°–75° C. at 1.5 mmHg to give 16.0 g of 1-carbomethoxypiperazine.

EXAMPLE 3

1-Carbomethoxy-4-[4,4-bis(p-fluorophenyl)butyl]piperazine hydrochloride

To a solution of 4.3 g (0.03 mole) 1-carbomethoxypiperazine in 10 ml of ethanol was added 10.0 g (0.036 mole) of 4-chloro-1,1-bis-(p-fluorophenyl)-butane and 5.0 g of sodium bicarbonate. The mixture was heated at reflux for 36 hours. 100 ml of water was added. The mixture was extracted twice with $Et_2O$. The combined extracts were dried over sodium sulphate and concentrated. The residue was dissolved in ethanol-ether and the hydrochloride was precipitated with ethanolic HCl. The solid was collected by filtration and recrystallised from propan-2-ol to give 2.2 g of 1-carbomethoxy-4-[4,4-bis(p-fluorophenyl)butyl]-piperazine hydrochloride. Melting point 192°–193° C.

EXAMPLE 4

1-Carboethoxy-4-[4,4-bis(p-fluorophenyl)butyl]piperazine hydrochloride

To a solution of 3.3 g (0.01 mole) of 1-[4,4-bis(p-fluorophenyl)butyl]piperazine in 10 ml of $CHCl_3$ was added dropwise over a period of 15 minutes 1.2 g (0.011 mole) of ethyl chloroformate in 10 ml of $CHCl_3$. The mixture was refluxed for 2 hours and was made basic with 0.8 g of sodium hydroxide in 25 ml of water.

The nonaqueous layer was separated, dried over sodium sulphate and concentrated. The residual oil was dissolved in ether and the hydrochloride was precipitated with ethanolic HCl. The solid was collected by filtration and recrystallised from 2-butanone-ether to give 3.0 g of 1-carboethoxy-4-[4,4-bis(p-fluorophenyl)-butyl]piperazine hydrochloride. Melting point 169°–70° C.

EXAMPLES 5–13

TABLE 3

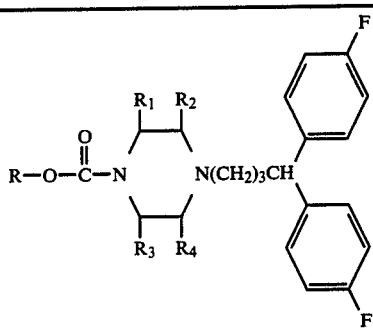

| Ex. | Method according to example | R | $R_1$–$R_4$ | M.p.[a] | Salt |
|---|---|---|---|---|---|
| 5 | 1, 2, 3 | $C_6H_5$ | $R_1$–$R_4$=H | 202–204° C. | HCl |
| 6 | 4 | n-$C_4H_9$ | $R_1$–$R_4$=H | 165–166° C. | $(COOH)_2$ |
| 7 | 4 | iso-$C_4H_9$ | $R_1$–$R_4$=H | 119–120° C. | HCl |
| 8 | 4 | $CH_2$–$C_6H_5$ | $R_1$–$R_4$=H | 179–180° C. | $(COOH)_2$ |
| 9 | 4 | $CH_3$ | $R_1$=$R_4$=$CH_3$(trans) $R_2$=$R_3$=H | 133–134° C. | $HCl.nH_2O$[b] |
| 10 | 4 | $C_2H_5$ | $R_1$=$R_4$=$CH_3$(trans) $R_2$=$R_3$=H | 116–117° C. | $HCl.nH_2O$[b] |
| 11 | 4 | $C_6H_5$ | $R_1$=$R_4$=$CH_3$(trans) $R_2$=$R_3$=H | 130–131° C. | HCl[c] |
| 12 | 4 | $CH_3$ | $R_1$=$R_3$=$CH_3$(cis) $R_2$=$R_4$=H | 164–165° C. | $(COOH)_2$ |
| 13 | 4 | $C_2H_5$ | $R_1$=$R_3$=$CH_3$(cis) $R_2$=$R_4$=H | 160–161° C. | $(COOH)_2$ |

[a]Melting points are uncorrected
[b]Slightly hygroscopic
[c]Contains some isopropanol.

We claim:

1. A compound of formula I:

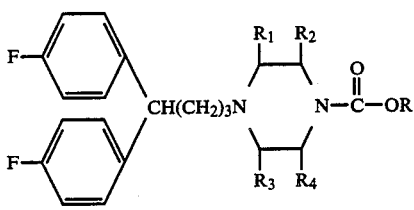

wherein R is alkyl straight or branch chained having from 1 to 10 carbon atoms, cycloalkyl having from 3 to 8 carbon atoms, aralkyl having from 7 to 9 carbon atoms or phenyl unsubstituted or substituted by one to three F, Cl, Br, lower alkyl having from 1 to 5 carbon atoms, lower alkoxy having from 1 to 5 carbon atoms, alkylenedioxy having from 1 to 3 carbon atoms, —$CF_3$ or —CN substituents, $R_1$–$R_4$ are independently H, $CH_3$, $C_2H_5$ with cis or trans configuration provided that only two of them are other than hydrogen, and provided that R is not ethyl when all of $R_1$–$R_4$ are hydrogen, and pharmaceutically acceptable salts thereof.

2. A compound according to claim 1, wherein two of $R_1$–$R_4$ are methyl.

3. A compound according to claim 1 wherein the compound is 1-carbomethoxy-4-[4,4-bis(p-fluorophenyl)butyl]-piperazine hydrochloride.

4. A pharmaceutical composition in dosage unit form which comprises from about 0.1 mg. to about 200 mg. of a compound of formula I as defined in claim 1 in combination with a conventional pharmaceutically acceptable carrier.

5. The composition according to claim 4 wherein two of the $R_1$–$R_4$ of the compound of formula I are methyl.

6. The composition according to claim 4 wherein the compound is 1-carbomethoxy-4-[4,4-bis(p-fluorophenyl)butyl]-piperazine hydrochloride.

* * * * *